United States Patent [19]

Kuijpers et al.

[11] Patent Number: 4,842,413
[45] Date of Patent: Jun. 27, 1989

[54] APPARATUS FOR ASSESSING THE WELD IN BELT LAYERS FOR RADIAL PNEUMATIC TIRES

[75] Inventors: Johannes A. M. Kuijpers, Dh Molenhoek; Piet van Berkum, Eb Apeldoorn; Henk Huisman, Da Epe, all of Netherlands

[73] Assignee: VMI EPE Holland B.V., Netherlands

[21] Appl. No.: 188,336

[22] Filed: Apr. 29, 1988

[30] Foreign Application Priority Data

Apr. 29, 1987 [NL] Netherlands ............... 8701019

[51] Int. Cl.⁴ .................................... G01N 21/89
[52] U.S. Cl. ............................... 356/426; 73/146; 250/572; 356/430; 356/237; 358/106
[58] Field of Search ........... 356/429, 430, 431, 237, 356/376, 426; 250/561, 571, 572; 358/106; 73/146

[56] References Cited

U.S. PATENT DOCUMENTS 3,926,704 12/1975 Sharp, Jr. ................... 73/146 X
4,277,178 7/1981 Cushing et al. ............. 356/431
4,543,602 9/1985 Kai et al. .................... 358/106

FOREIGN PATENT DOCUMENTS 59-136606 6/1984 Japan.
2157419 10/1985 United Kingdom.

OTHER PUBLICATIONS

Japan Patent Abstract, vol. 8, No. 269 (P-319) (1706) dated Dec. 8, 1984.
Dr. G. Seger et al., "Qualitätskontrole Durch Automatisierte Sichtprüfung", pp. 312-316, Messin+-Prüfen/Automatik, vol. 20, No. 6, Jun. 1984, (Bad Wörishofen, DE).

*Primary Examiner*—Vincent P. McGraw
*Attorney, Agent, or Firm*—Pennie & Edmonds

[57] ABSTRACT

Apparatus for assessing the weld in a belt layer for a radial pneumatic tire in which the belt layer has been disposed onto a rotary drum, comprising an apparatus for directing at least one laser beam towards the drum and the belt layer, said laser beam being directed obliquely with respect to the perpendicular on the belt layer and the drum, and a camera for viewing the position of the projection of the laser beam on the drum and the belt layer.

12 Claims, 1 Drawing Sheet

APPARATUS FOR ASSESSING THE WELD IN BELT LAYERS FOR RADIAL PNEUMATIC TIRES

The invention relates to an apparatus for assessing the weld in a belt layer for a pneumatic tyre in the assembling stage, the belt layer having been disposed onto a rotary drum.

Each radial pneumatic tyre comprises a belt that consists of at least one layer that is formed of a strip of a rubber mixture with cords embedded therein, said cords being e.g. of steel, aramid, rayon, fibre glass, in which cords of different materials can be applied in one belt structure. The belt is constructed by laying strips one after another about a cilindrical drum after the lengths of the strips have been cut to size, so that the ends of each strip end up adjacent to each other on the drum in order to form a belt weld. Usually the ends of the strips have been cut obliquely with respect to the centre line of the strip.

A perfect belt weld is characterized in that:

(1) the ends of the strip on the drum are butted, so that the ends do not overlap but are not interspaced either.

(2) the centre line of the strip should not stagger at the weld, so that the strip, viewed from its one end has to be disposed in line with the strip at its other end.

(3) the strip should not be thicker or thinner at the weld than in any other part of the strip.

(4) the cords on either side of the weld should be parallel to one another, i.e., they are not supposed to cross one another. Moreover the distance between the cords on either side of the weld should be equal to the distance between each pair of adjacent cords that are disposed elsewhere in the strip. The result should be such that upon X-ray examination of steel-wire cords the weld cannot be localized. In this situation the ends of the strip extend obliquely with respect to the centre line of the strip and the cords extend parallel to said ends.

However, practice teaches that a belt weld with the above-mentioned perfect properties is not always easy to obtain, so that a person's interference is required by sometimes difficult remodelling and/or re-arranging of the ends of the strip with respect to each other so as to obtain something that looks like a better weld. These remodelling and/or re-arranging operations are possible due to the fact that the rubber has not yet vulcanized and thus is kneadable. These remodelling and/or re-arranging operations comprise actions such as stretching a strip to close an open weld or compacting a strip at an overlapping weld or laying the ends of the strip in line with each other. It is also possible that the equipment for cutting the lengths of strips has been incorrectly adjusted, or that the position of the pointed beginning in the belt layer material and the pointed end results in a low-grade weld.

Therefore it is that person who determines whether a weld, possibly after correction, is of acceptable quality to be admitted to the assembling stage so as to produce a radial pneumatic tyre. After assembly the quality of the weld can no longer be checked visually since the subsequent belt layers have been disposed as a radial tyre usually comprising more than one belt layer and/or since the tread has been disposed onto the belt, so that the belt layer weld can no longer be seen. Therefore the quality of the weld depends on the judgment of the person operating the machine and his ability to correct, and on the adjustment of the equipment that cuts the strips of belt material.

However, faulty welds have a very unfavourable influence on the performance, safety and life span of the radial pneumatic tyre, substantially in the following manner:

(1) an outwardly sound-looking, new radial pneumatic tyre could cause vibrations or even shocks at rolling contact with a road surface by variations in that contact due to irregularities in the belt layers. This is annoying to people travelling in a motor car and therefore the qualifications that motor car manufacturers demand of tyre suppliers become increasingly more severe.

(2) a pneumatic tyre can at a random point in its life span start to show accelerated and/or irregular wear due to irregularities in the belt layers. Particularly the lack of cords or the presence of overlaps at the belt welds are feared defects that influence the practical reliability and the safety. Not only is it so that locally accelerated or irregular wear has a negative influence on driving comfort and braking distance, but bad belt welds can also lead to losening and complete disintegration of the belt layers.

(3) if the symptoms described above sub (1) and (2) have not resulted in complaints by non-critical users, a faulty weld is still unfavourable when it comes to giving a tyre a second life by recovering the tread. Since radial pneumatic tyres are often manufactured with steel cords in the belts, examination by means of X-rays is an often applied selection method to preven tyres with bad belt welds and/or with the first signs of losening to be recovered with a new tread.

Faulty welds, i.e. the above-mentioned open welds, overlapping welds or welds with crossing cords, can be detected with the aid of X-rays after vulcanization if steel cords have been applied. However, since cords of rayon or aramide or fibre glass etc. are also applied, which cannot be made clearly visible or cannot be made visible at all with the aid of X-rays, the wish to be able to assess welds in the building stage of the belt on the tyre-building machine has long been in existence, for only at that stage it can be prevented that tyres having bad welds subsequently get the chance to make it through inspection.

Therefore the invention aims to provide an apparatus that enables the assessing of welds in belt layers during the building or assembling stage, no matter whether they comprise cords made of steel or synthetic fibres or a combination of the two. Shifting the inspection of a tyre from the point at which it is usually done, viz. after vulcanization, to the moment at which the belt is created during building, not only reduces the number of tyres with dubious to faulty welds that gets onto the road, but also reduces the number of bad tyres that is able to reach the vulcanization department.

This invented equipment is substantially characterized by an apparatus for directing at least one laser beam towards the drum and the belt layer, said laser beam being directed obliqely with respect to the perpendicular on the belt layer and the drum and by a camera for viewing the position of the projection of the laser beam on the drum and the belt layer.

The invention will be further elucidated in the following description of a quite schematic example of an embodiment, starting from the most common belt construction, viz. a belt having two layers of cords either made of steel or aramide or rayon etc. that are disposed at an angle with respect to the center line of the belt layer, whereas the angles of the two belt layers are opposite to one another. This description refers to the enclosed drawings wherein.

Any pneumatic tyre for vehicles comprises i.a. a belt that consists of at least one layer, each belt layer comprising a strip with ends cut obliquely with respect to the centre line of the strip. This strip is placed on a cilindrical drum, the ends butting so as to obtain a perfect weld. The strip comprises cords, which can be of steel wire, embedded in rubber. Such a radial pneumatic tyre is commonly known and therefore it is not discussed further, nor has it been drawn.

In a perfect belt weld the ends of the strip should be butting each other, so that the ends do not overlap but are not interspaced either. Moreover the centre line of the strip should not stagger, so that the strip viewed from the one end is supposed to lie perfectly in line with the other end. Furthermore the strip should not be thicker or thinner at the weld than at other parts of the strip. Furthermore the cords on either side of the weld should be parallel to one another so they should not cross one another. Finally the distance between any pair of adjacent cords should be the same, also at the welds.

However, practice teaches that a belt weld with the above-mentioned perfect properties is not always easy to obtian, so that a person's interference is required by sometimes laborious remodelling and/or re-arranging of the ends of the strip with respect to each other so as to obtain something that looks like a better weld. These remodelling and/or re-arranging operations comprise actions such as stretching a strip at an open weld or compacting a strip at an overlapping weld, since the rubber has not yet vulcanized and thus is kneadable, while by re-arranging the the ends the strips can be laid in line with each other.

Therefore that person determines whether the weld, possible after correction, is acceptable for further processing in the building stage to a radial pneumatic tyre. Up to now, after vulcanization of the tyres, the quality of welds in their belt material could only be assessed by means of X-rays and then only if the belt has cords of steel.

For that reason the invention aims to provide an apparatus that enables the assessing of the quality of belt welds on the building equipment even if the applied belt layers comprise cords of synthetic fibres.

Figure 1:
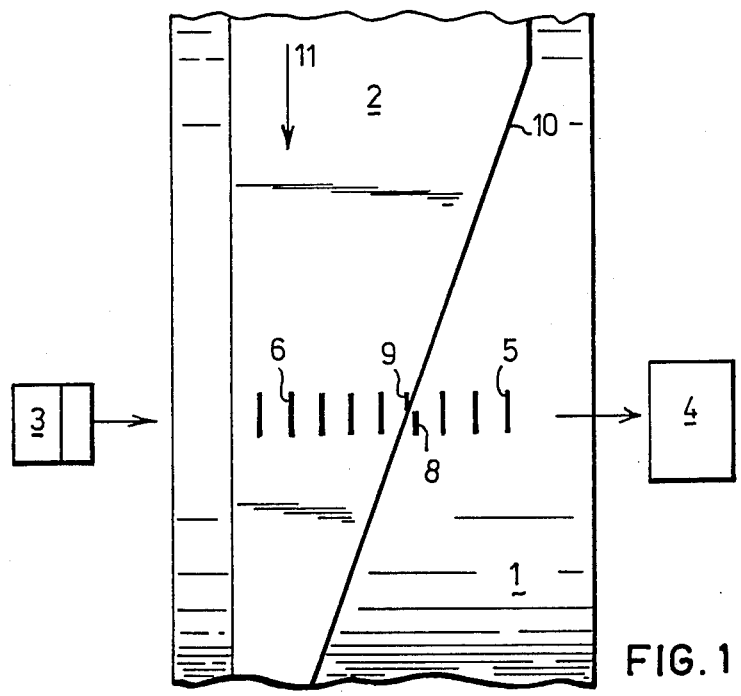
FIG. 1 is a schematic plan view of the invented apparatus.
Figure 2:
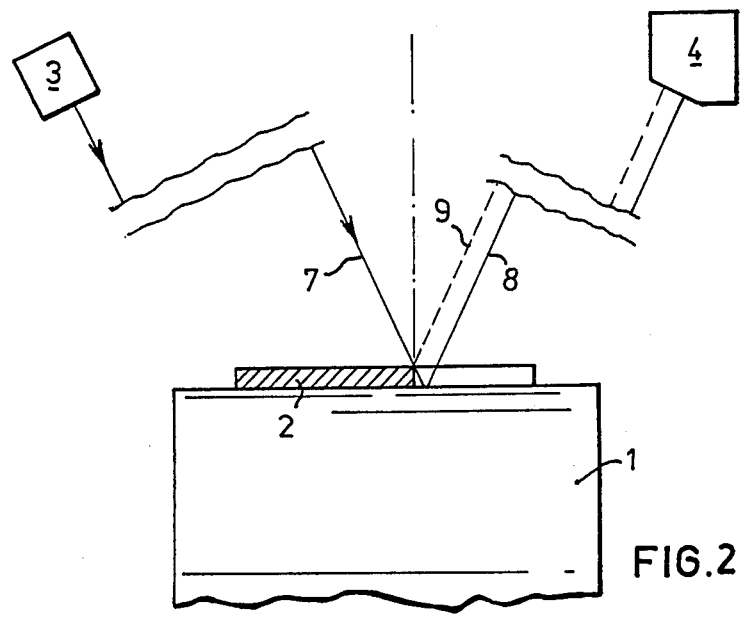
FIG. 2 is a schematic cross-section through the row of laser projections according to FIG. 1.
Figure 1:
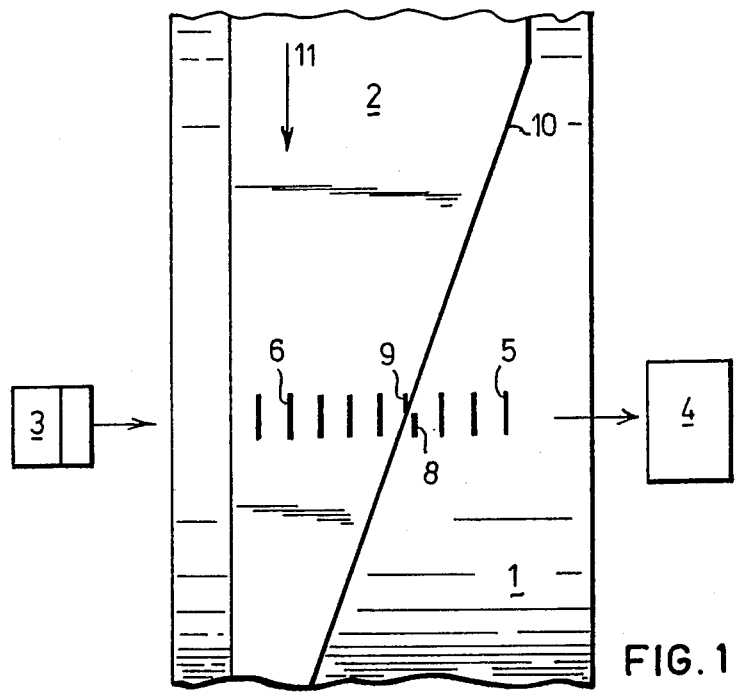
Figure 2:
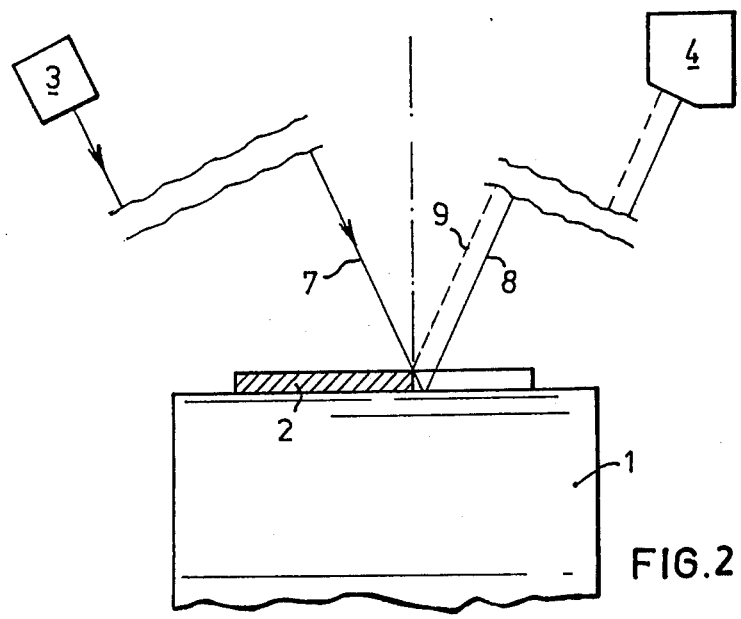

The invented apparatus is shown very schematically in FIGS. 1 and 2. In this embodiment, a rubber strip 2 to be processed into a belt and incorporating cords either of steel or of synthetic material is disposed on a drum 1 for building a belt for a radial pneumatic tyre. For clarity's sake in FIGS. 1 and 2 only one end of the strip 2 has been drawn and large parts of the drum, which is known per se, have been omitted. In FIGS. 1 and 2 the axis of the drum extends horizontally in the plane of the drawing and the centre line of the strip extends vertically in the plane of the drawing in FIG. 1 but is perpendicular to the plane of the drawing in FIG. 2. The other end of the strip should be butted to the edge 10 to be welded, but has been omitted for clarity's sake.

By means of a device 3 for transmitting laser beams, being shown very schematically in FIGS. 1 and 2 and being known per se so that it needs not be discussed here, laser beams are transmitted to the strip 2 and the drum 1 at an angle of e.g. 25° with respect to the perpendicular on the strip 2 and the drum 1. Thus e.g. eight laser beam projections 5, 6, 8, 9 are created in a row perpendicularly to the length of the strip 2 according to FIG. 1. The mutual distance between the projections is e.g. 20 mm. Each laser beam is preferably strip-shaped with a length of e.g. 5 mm and a width of e.g. 1 mm, the projections being mutually parallel. The drum 1 and therefore also the strip 2 rotate at a speed of 50 rev. per minute, so that FIGS. 1 and 2 only show an instantaneous indication, in which according to FIG. 1 at that instant five projections 6 are completely disposed on the shown end of the strip 2, but three projections 5 are disposed beyond the shown end of the strip.

Between the projections 6 on the strip 2 and the projections 5 disposed beyond the edge 10 of the strip 2 shown in FIG. 1 there is a projection that is partly on the strip 2, viz. part 9, whereas the rest of this projection, viz. part 8, is not on the drawn end of strip 2. It appears from FIG. 2 why FIG. 1 shows part 8 shifted with respect to part 9, since the laser ray 7, by inciding obliquely onto the drum, travels a longer way the drum 1 than to the strip 2.

Projections 5, 6, 8 and 9 are viewed by a camera 4, being a linary CCD camera that is known per se and therefore needs not be described further. The camera is directed at an angle of e.g. 25° with respect to the entire width of the drum and thus has been indicated quite schematically in FIGS. 1 and 2. This camera 4 records that the projections 6, and also the projections 5, look normal, but that the intermediate projection is divided in a part 9 and, shifted with respect thereto, a part 8, so that the camera records the position of the edge 10 of the belt strip 2 by the projection 8, 9. As explained above and as appears from FIG. 2 the camera records differences in level that are indicated by shifted position of the part 8 with respect to the the part 9 in one and the same projection, but also by the shifted position of the projections 5 with respect to the positions they would assume if the projections 5 would be disposed on the belt strip 2.

Because the drum 1 rotates, the belt 2 moves in the direction of the arrow 11 so that all the projections 6 and 5 shift partially from the right to the left in FIG. 1 due to the passing of the edge 10 of the strip 2, thus enabling the linary CCD camera to record the position of the entire edge 10 of the strip 2. In an analogue manner the camera scans the edge of the other end of strip 2, i.e. in FIG. 1 with the projections 5, so that the distance between the two ends of the strip 2 is recorded. If the two ends of the belt strip 2 are not in butting position, but leave a part of the drum 1 exposed, then shifting of the projections occurs as with the projection parts 8 and 9.

If the ends of the belt strip 2 overlap, this also appears from the position of the projections 5, 6 and then this position is also recorded by camera 4. The edge 10 of the downwardly extending end of the strip 2 in FIG. 1 is then disposed over the other end of the strip 2, which end has not been drawn but which will extend upwardly in FIG. 1. Thereby part 8 of the projection is then also shifted with respect to the part 9. However, the projections 6 and 9 are disposed even higher than indicated in FIGS. 1 and 2, so that the camera records them as having been shifted to the left with respect to the standard, i.e. the projections on the drum. The projections 5 and 8 are then disposed on the strip 2 and are thus higher than the surface of the drum and therefore they are recorded as having been shifted to the left with respect to the standard, i.e. the projections on the drum. It is also possible that the two end edges of the strip 2 cross each other, which will appear from shifted projections. How those projections have shifted can be easily derived from the above and from FIGS. 1 and 2 so that it is not explained here.

The linearly CCD camera can be connected to a processor, which is known per se and therefore not discussed here, with which the length of the opening between the ends of the belt strip or the overlap of these ends is indicated. The speed with which the camera records can e.g. be such that each time after passing about 0.1 mm of the strip the position of the projections is recorded. However, the processecor can also be set to a 0.5 mm tolerance. If the maximum admissable weld opening is 2 mm, the processor should thus be set to accept weld openings of 1.5 mm at the most. At 50 revolutions per minute this cannot be perceived by the human eye, so that the invented apparatus is an important means for detecting faulty welds.

The admissable width of an open or overlapping weld depends on the standards of the tyre manufacturer and is expressed in millimeters or number of cords. Also the number of admissable crossing cords, a phenomenon occurring when the end edges of the strip cross, depends on the tyre manufacturer.

The invented system completely replaces the surveying to be performed by a person and is thus free of subjectivity. It provides constant examination without touching the belt and at a high level of accuracy. The measurings are collected and assessed fast so that the operator can take immediate action, while a great number of belts per time unit can be checked.

The systems measures differences in height and therfore it can also be applied for other purposes, e.g. for:

(1) checking whether the end parts of the belt are in line with one another;

(2) checking whether the longitudinal edges of the belt do not sway over the width of the drum;

(3) checking whether the rest of the belt, i.e. apart from the weld, has a constant thickness, e.g. is not creased or has other defects;

(4) checking whether the weld in the tread (which is not the belt) is open or overlapping;

(5) controlling the cutting of strips from large sheets of belt material and/or the subsequently welding the cut strips to a long material band from which the pieces of belt strip are cut.

The apparatuses for these other applications can easily be derived from the above-described apparatus so it is not necessary to describe or draw them here.

We claim:

1. Apparatus for assessing the weld in a belt layer for a radial pneumatic tyre in which the belt layer has been disposed onto a rotary drum, characterized by an apparatus for directing at least one laser beam towards the drum and the belt layer, said laser beam being directed obliquely with respect to the perpendicular on the belt layer and the drum and by a camera for viewing the postition of the projection of the laser beam on the drum and the belt layer.

2. Apparatus according to claim 1, characterized in that the laser beam or beams enclose a 25° angle with the perpendicular on the belt layer and the drum.

3. Apparatus according to claim 1, characterized in that the apparatus directs laser beams towards the belt layer and the drum, each beam exposing a strip-shaped area on the drum and/or belt layer.

4. Apparatus according to claim 3, characterized in that the strips are parallel to one another and have been disposed transversely to the centre line of the belt layer.

5. Apparatus according to claim 3, characterized in that each strip has a length of 5 mm.

6. Apparatus according to one of claim 3, characterized in that each strip has a width of 1 mm.

7. Apparatus according to one of claim 6, characterized in that the mutual distance between two adjacent strips can be adjusted to e.g. 20 mm.

8. Apparatus according to one of claim 7, characterized in that the number of strips is eight.

9. Apparatus according to claim 8, characterized in that the drum is rotated at a speed of 50 revolutions per minute.

10. Apparatus according to any of claims 1 and 9, characterized in that the camera is directed along a line that is oblique with respect to the perpendicular on the drum and belt layer towards the projection(s) of the laser beams on the drum and/or belt layer.

11. Apparatus according to claim 10, characterized in that the camera is a lineary CCD camera.

12. Apparatus according to claim 11, characterized in that the camera is connected to a processor.

* * * * *